(12) United States Patent
Shaver (10) Patent No.: US 8,563,772 B2
(45) Date of Patent: Oct. 22, 2013

(54) METHANOL CARBONYLATION WITH IMPROVED ALDEHYDE REMOVAL

(75) Inventor: Ronald D. Shaver, Houston, TX (US)

(73) Assignee: Celanese International Corp., Irving, TX (US)

( * ) Notice: Subject to any disclaimer, the term of this patent is extended or adjusted under 35 U.S.C. 154(b) by 464 days.

(21) Appl. No.: 12/930,363

(22) Filed: Jan. 5, 2011

(65) Prior Publication Data

US 2011/0112324 A1    May 12, 2011

Related U.S. Application Data

(62) Division of application No. 12/291,310, filed on Nov. 7, 2008, now Pat. No. 7,884,237.

(51) Int. Cl.
*C07C 51/12* (2006.01)
(52) U.S. Cl.
USPC ............................................. 562/519
(58) Field of Classification Search
None
See application file for complete search history.

(56) References Cited

U.S. PATENT DOCUMENTS

| | | | |
|---|---|---|---|
| 2,938,017 A | 5/1960 | Grosser | 260/88.3 |
| 5,001,259 A | 3/1991 | Smith et al. | 562/519 |
| 5,026,908 A | 6/1991 | Smith et al. | 562/519 |
| 5,144,068 A | 9/1992 | Smith et al. | |
| 5,334,755 A | 8/1994 | Yoneda et al. | 562/519 |
| 5,466,874 A | 11/1995 | Scates et al. | 562/519 |
| 5,696,284 A | 12/1997 | Baker et al. | 560/232 |
| 5,756,836 A | 5/1998 | Shimizu et al. | 562/519 |
| 5,770,768 A | 6/1998 | Denis et al. | 562/519 |
| 5,877,347 A | 3/1999 | Ditzel et al. | 562/519 |
| 5,877,348 A | 3/1999 | Ditzel et al. | 562/519 |
| 5,883,295 A | 3/1999 | Sunley et al. | 562/519 |
| 5,932,764 A | 8/1999 | Morris et al. | 562/519 |
| 5,942,460 A | 8/1999 | Garland et al. | 502/150 |
| 6,143,930 A | 11/2000 | Singh et al. | 562/608 |
| 6,339,171 B1 | 1/2002 | Singh et al. | 562/519 |
| 6,627,770 B1 | 9/2003 | Cheung et al. | 562/519 |
| 2002/0151746 A1 | 10/2002 | Scates et al. | 562/519 |
| 2005/0197513 A1 | 9/2005 | Trueba et al. | 568/492 |
| 2007/0225521 A1 | 9/2007 | Torrence | 562/519 |

FOREIGN PATENT DOCUMENTS

| | | |
|---|---|---|
| CN | ZL92108244.4 | 6/1999 |
| DD | 2059484 | 6/1972 |
| EP | 0 161 874 A1 | 11/1985 |
| EP | 0 759 419 A1 | 2/1997 |
| EP | 0 849 248 A1 | 6/1998 |
| WO | WO 2008/133816 A1 | 11/2008 |

OTHER PUBLICATIONS

Research Report from 2006 Forum of the Southwest Research & Design Institute of Chemistry Industry (slides 1-32), entitled "Process of 200ktpa Methanol Low Press Oxo Synthesis AA"; and Jane H. Jones, "The Cativa Process for the Manufacture Plant of Acetic Acid, Platinum Metals Review", Johnson Matthey, SA, vol. 44, No. 3, Jan. 1, 2000, pp. 94-105.

*Primary Examiner* — Yevegeny Valenrod
(74) *Attorney, Agent, or Firm* — Michael W. Ferrell (57) ABSTRACT

Methanol carbonylation with improved aldehyde removal includes: (a) scrubbing light ends and aldehyde impurity from vent gas with an absorber solvent; (b) stripping absorbed light ends and aldehyde impurity from the absorber solvent to provide a vent-recovered light ends stream; (c) purifying the vent-recovered light ends stream to remove aldehyde impurity; and (d) recycling purified light ends from the vent-recovered light ends stream to the production system.

15 Claims, 5 Drawing Sheets

METHANOL CARBONYLATION WITH IMPROVED ALDEHYDE REMOVAL

CROSS REFERENCE TO RELATED CASE

This application is a Divisional Application of U.S. patent application Ser. No. 12/291,310, entitled "Methanol Carbonylation With Improved Aldehyde Removal", filed Nov. 7, 2008, now U.S. Pat. No. 7,884,237. The priority of U.S. patent application Ser. No. 12/291,310 is hereby claimed and its disclosure incorporated herein by reference in its entirety.

FIELD OF THE INVENTION

The present invention relates to the manufacture of acetic acid and more particularly to acetic acid manufacture with improved aldehyde removal.

BACKGROUND

Among currently employed processes for synthesizing acetic acid, one of the most used commercially is the catalyzed carbonylation of methanol with carbon monoxide. Preferred methods of practicing this technology include so-called "low water" processes catalyzed with rhodium or iridium of the class seen in commonly assigned U.S. Pat. No. 5,001,259, issued Mar. 19, 1991; U.S. Pat. No. 5,026,908, issued Jun. 25, 1991; and U.S. Pat. No. 5,144,068, issued Sep. 1, 1992; as well as European Patent No. EP 0 161 874 B2, published Jul. 1, 1992. The features involved in practicing a low water carbonylation process may include maintaining in the reaction medium, along with a catalytically effective amount of rhodium and at least a finite concentration of water, an elevated concentration of inorganic iodide anion over and above the iodide ion that is present due to hydrogen iodide in the system. This iodide ion may be a simple salt, with lithium iodide being preferred in most cases. U.S. Pat. Nos. 5,001,259, 5,026,908, 5,144,068 and European Patent No. EP 0 161 874 B2 are herein incorporated by reference.

It has been found that although a low water carbonylation process for producing acetic acid increases carbon monoxide efficiency by reducing by-products carbon dioxide and hydrogen, the amount of other impurities, such as acetaldehyde and its derivatives, increase in a low water carbonylation process as opposed to similar processes operated with higher water concentrations in the reactor. These impurities affect quality of acetic acid, especially when they are recirculated through the reaction process which causes build up of derivative impurities, such as carbonyl compounds and alkyl iodides. Carbonyl impurities decrease the permanganate time of the acetic acid, a quality test commonly used in the industry. As used herein, the phrase "carbonyl" is intended to mean compounds that contain aldehyde or ketone functional groups, which compounds may or may not possess unsaturation. See Catalysis of Organic Reaction, 75, 369-380 (1998), for further discussion on impurities in a carbonylation process.

The present invention is directed, in part, to reducing and/or removing permanganate reducing compounds (PRC's) such as acetaldehyde, acetone, methyl ethyl ketone, butyraldehyde, crotonaldehyde, 2-ethyl crotonaldehyde, and 2-ethyl butyraldehyde and the like, alkyl iodides that may be derived from acetaldehyde and the aldol condensation products of the impurities. The present invention may also lead to reduction of propionic acid formation in some cases because acetaldehyde formation appears to cause increases in propionic acid levels, perhaps because of the availability of hydrogen in the reactor. Without intending to be bound by theory, it is believed that many impurities are derived from acetaldehyde which appears to form more readily in the presence of iodide salts, for example, lithium iodide. Acetaldehyde condenses to form unsaturated aldehydes, such as crotonaldehyde, which may then generate higher alkyl iodides in the system which are particularly difficult to remove and are poisonous to vinyl acetate catalysts. Vinyl acetate production is the single largest end-use of acetic acid.

Conventional techniques to remove acetaldehyde impurities include treating the acetic acid product streams with low concentrations of aldehyde impurity with oxidizers, ozone, water, methanol, activated-carbon, amines, and the like. Such treatments may or may not be combined with distillation of the acetic acid. The most typical purification treatment involves a series of distillations of the final product. It is also known to remove carbonyl impurities from organic streams by treating the organic streams with an amine compound such as hydroxylamine, which reacts with the carbonyl compounds to form oximes, followed by distillation to separate the purified organic product from the oxime reaction products. However, the additional treatment of the final product adds cost to the process, and distillation of the treated acetic acid product can result in additional impurities being formed.

Other processes have been described for producing high purity acetic acid by distilling light ends condensed from the light ends stripper column to remove acetaldehyde. Streams suggested for processing to remove acetaldehyde include a light phase containing primarily water, acetic acid and methyl acetate; or a heavy phase containing primarily methyl iodide, methyl acetate and acetic acid; or a stream formed by combining the light and heavy phase. It has been disclosed, for example, in commonly assigned U.S. Pat. Nos. 6,143,930 and 6,339,171, that it is possible to significantly reduce the undesirable impurities in the acetic acid product by performing a multi-stage purification on the condensed light ends column overhead. These patents disclose a purification process in which the light ends overhead is distilled twice, in each case taking the acetaldehyde overhead and returning a methyl iodide rich residuum to the reactor. The acetaldehyde-rich distillate obtained after the two distillation steps is optionally extracted with water to remove the majority of the acetaldehyde for disposal, leaving a significantly lower acetaldehyde concentration in the raffinate that is recycled to the reactor. U.S. Pat. Nos. 6,143,930 and 6,339,171 are incorporated herein by reference in their entirety. Additional systems for removing aldehydes and other permanganate reducing compounds are described in U.S. patent application Ser. No. 11/116,771 (Publication No. US 2006/0247466 A1) of Zinobile et al., entitled "Process for the Production of Acetic Acid"; U.S. patent application Ser. No. 10/708,420 (Publication No. US 2005/0197508 A1) of Scates et al., entitled "Removal of Permanganate Reducing Compounds from Methanol Carbonylation Process Stream"; and U.S. patent application Ser. No. 10/708,421 (Publication No. US 2005/0197509 A1) of Picard et al., entitled "Removal of Permanganate Reducing Compounds from Methanol Carbonylation Process Stream"; the disclosures of which are hereby incorporated by reference. In general, the condensed light ends contain less than 1 weight percent acetaldehyde.

While the above-described processes have been successful in removing carbonyl impurities from the carbonylation system and controlling acetaldehyde levels and permanganate time, existing procedures tend to be expensive in terms of both capital and operating costs due to the low levels of aldehyde impurity that need to be removed from a particular stream to prevent build-up of aldehyde and related impurities in the system. Accordingly, there remains a need for alternative processes to improve the efficiency of acetaldehyde removal in methanol carbonylation processes.

SUMMARY OF THE INVENTION

In accordance with the invention, a vent gas light ends recovery absorber system is utilized to collect acetaldehyde in a recovered light ends stream stripped from the absorber fluid. The vent-recovered light ends stream is purified by removing acetaldehyde prior to returning the recovered light ends to the carbonylation system. The improvement thus includes generally (a) scrubbing light ends and aldehyde impurity from vent gas with an absorber solvent; (b) stripping absorbed light ends and aldehyde impurity from the absorber solvent to provide a recovered light ends stream with acetaldehyde impurity; (c) purifying the recovered light ends stream to remove aldehyde impurity; and (d) recycling purified light ends from the recovered light ends stream to the production system.

The recovered light ends stream may contain greater than 1 up to 5% or more acetaldehyde by weight which greatly reduces the volume of light ends that need to be purified of aldehydes in order to remove them from a carbonylation system. That is, existing systems teach to treat streams which contain acetaldehyde at less than 10,000 ppm. Operating and capital costs for removing comparable amounts of acetaldehyde with the approach of this invention are accordingly dramatically lower than the prior art methodologies described above because the volume of light ends that need to be purified to remove a given amount of acetaldehyde impurity is greatly reduced. Preferably, acetaldehyde is present in the recovered light ends by at least 2 or 3 weight percent with up to 5 weight percent or more. From 2-10 weight percent concentration of acetaldehyde in a recovered light ends stream may be achieved in connection with a particular design.

Further features and advantages of the present invention will become apparent from the discussion which follows.

BRIEF DESCRIPTION OF DRAWINGS

The invention is described in detail below with reference to the various figures wherein like numerals designate similar parts. In the Figures.

DETAILED DESCRIPTION

The invention is described in detail below with reference to several embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. % and like terms, for example, refer to weight percent, unless otherwise indicated.

"Aldehyde impurity" refers to acetaldehyde and related compounds which may be present in vent gas.

"Light ends" refers to reaction mixture components which are more volatile than acetic acid. Typically, "light ends" refers to methyl iodide and methyl acetate which are the predominant components.

"Stripping" refers to removing a component from a mixture by evaporation or distillation.

Referring to FIGS. 1, 2, 4 and 5 there is shown a carbonylation system 10 of the class described above used for producing acetic acid. System 10 includes a reactor 12, a flasher 14, a light ends or stripper column 16, a drying column 18, and optionally includes further purification of the drying column residue product. The reactor vent may be sent to a high pressure absorber or other equipment as is known. See Chinese Patent No. ZL92108244.4, as well as European Patent No. EP 0 759 419 and U.S. Pat. No. 5,770,768 to Denis et al., the disclosures of which are hereby incorporated by reference. Also included in system 10 is a low pressure absorber tower shown at 26 and a vent stripper column shown at 28.

In order to produce acetic acid, methanol and/or a reactive derivative such as methyl acetate and carbon monoxide are fed to reactor 12 which contains a homogeneous, metal catalyzed reaction medium. As the methanol or its reactive derivatives are carbonylated, a portion of the reaction mixture is drawn from the reactor and fed via line 30 to flasher 14. In the flasher, there exists a reduced pressure relative to the reactor such that a crude product stream 34 is produced by flashing. Stream 34 is fed to light ends or stripper column 16 as shown in the diagram. The catalyst fed to flasher 14 is recycled via line 36 to reactor 12.

In light ends column 16, crude product stream 34 is further purified. In particular, the light ends are distilled from column 16 to overhead 38. Overhead 38 consists predominantly of methyl iodide and methyl acetate, which is condensed at condenser 40 and fed to a receiver vessel 42. From receiver vessel 42, the condensed material is decanted and used as recycle as indicated at lines 44, 46 and 48.

Reflux is also drawn from receiver 42 and provided to light ends column via line 50.

Figure 1:
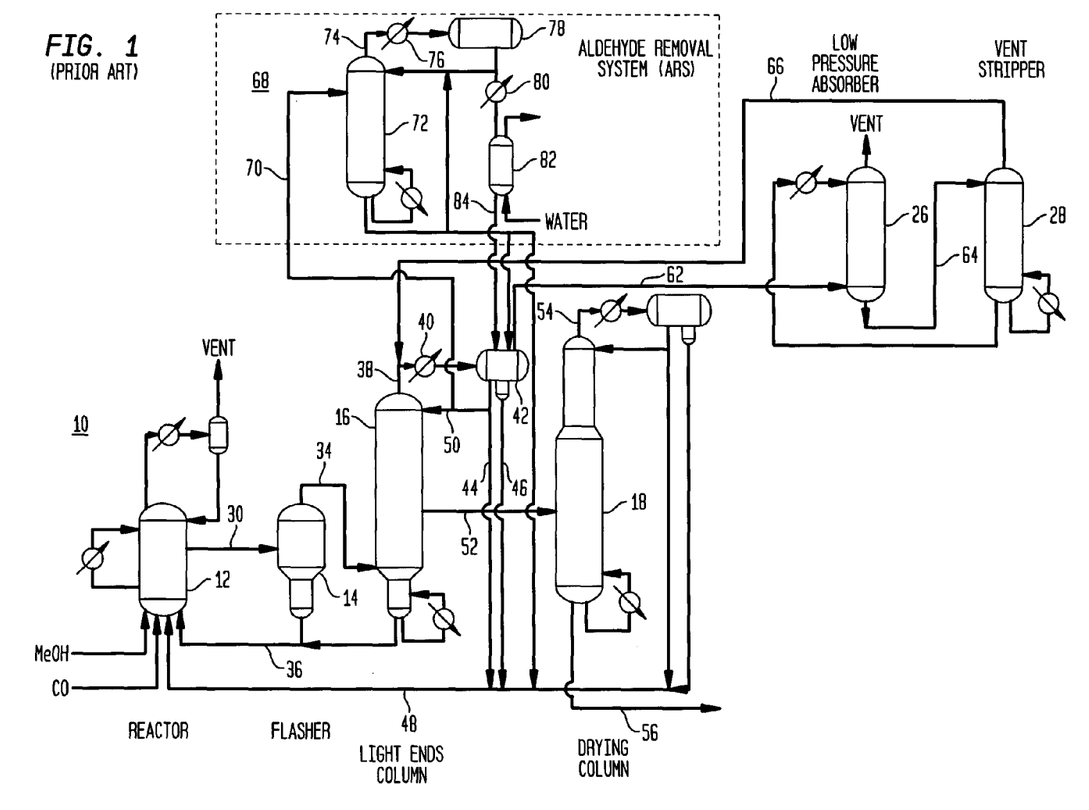
FIG. 1 is a schematic diagram of a methanol carbonylation system having a conventional aldehyde removal system.
Figure 2:
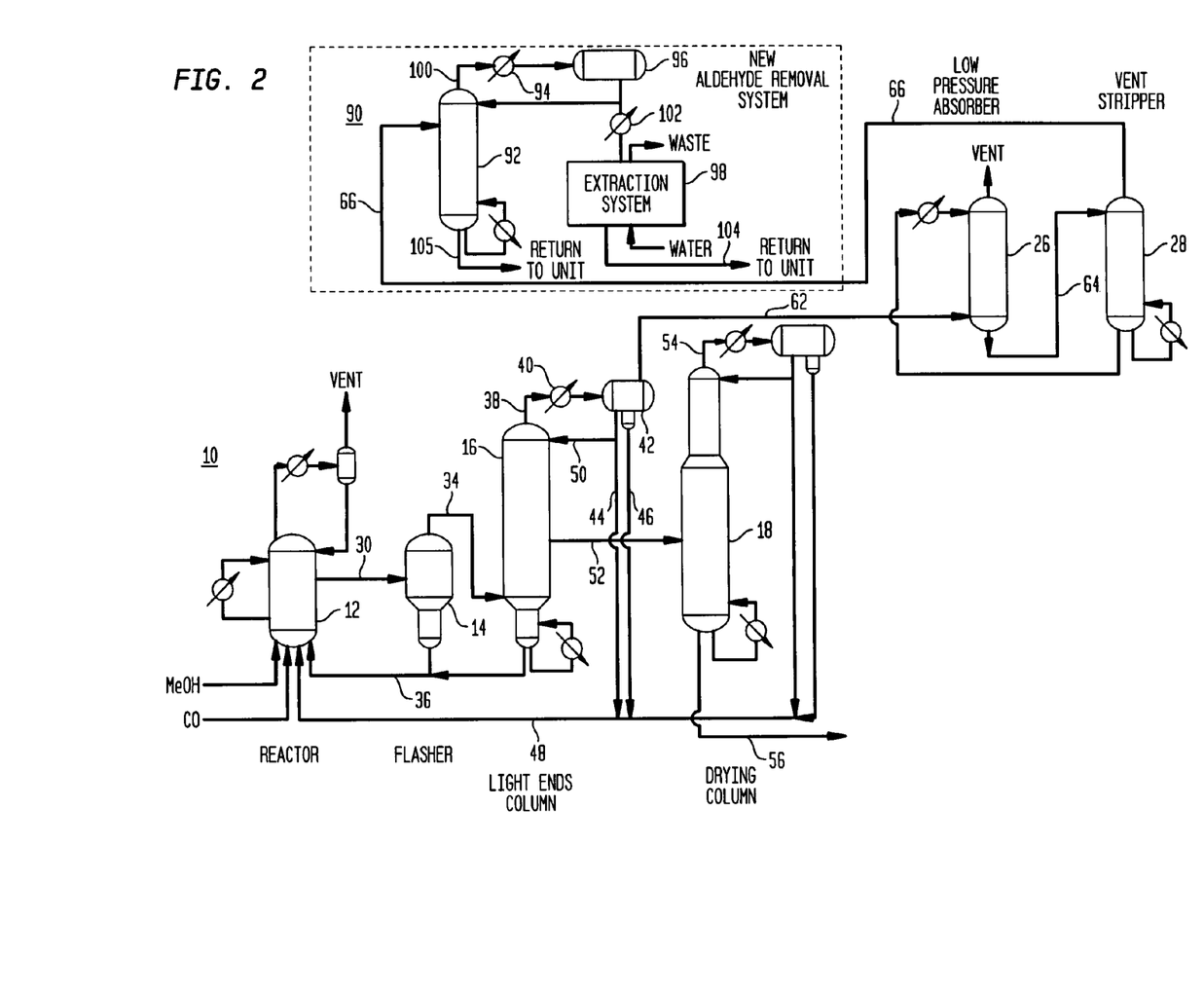
FIG. 2 is a schematic diagram of a methanol carbonylation system of the present invention, having an aldehyde removal system coupled to the vent gas stripper in accordance with the present invention.

A side stream 52 is drawn from stripper column 16 and fed to dehydration column 18 as shown in the diagrams of FIGS. 1 and 2 via line 52. Line 52 represents a purified product stream, that is, wherein the methyl iodide and methyl acetate have been substantially removed. However, the composition of stream 52 contains substantial amounts of water, which is why drying column 18 is employed. In drying column 18, water is removed via overhead 54 and recycled as shown. Product leaves drying column 18 via line 56 and is optionally fed to further purification for removal of heavy ends and iodine containing impurities before being sent to product storage.

Referring specifically to FIG. 1, there is shown a conventional configuration, wherein vent gas from receiver 42 is fed to absorber tower 26 via line 62. In tower 26, the vent gas supplied via line 62 is scrubbed with chilled acetic acid which, after use, is fed to vent stripper tower 28 via line 64. The stripped vapor, containing methyl iodide and methyl acetate, is re-fed to the light ends section via line 66 so that the methyl iodide and methyl acetate are recycled.

The aldehyde removal system shown schematically at 68 operates on either a light phase or a heavy phase drawn from receiver vessel, 42 as shown at 70. In aldehyde removal system 68, the condensed liquid from the receiver vessel fed via line 70 is subjected to a distillation in column 72 to remove acetaldehyde and optionally other permanganate reducing compounds, as is known in the art. The purified residue of column 72 is returned to the production unit as shown. The overhead, containing light ends, acetaldehyde and other permanganate reducing compounds is taken as overhead in line 74. The overhead is condensed at 76 and fed to a receiver 78. The material may be further cooled at 80 before the permanganate reducing compounds are extracted from the condensed liquid in extractor 82. The purified overhead material, i.e. having acetaldehyde removed, is returned to receiver 42 via line 84 as shown in the diagram.

Figure 3:
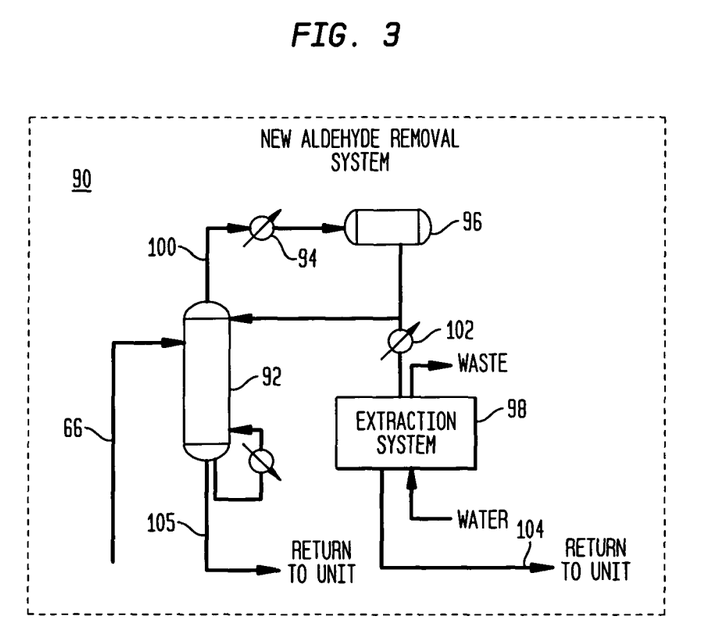
FIG. 3 is an enlarged detail showing the aldehyde removal system of FIG. 2.

The improvement of the current invention is illustrated in FIGS. 2 and 3.

In FIGS. 2 and 3, vent gas is likewise fed to absorber tower 26 from receiver vessel 42 via line 62. In column 26, the vent gas is scrubbed with chilled acetic acid which, after use, is fed via line 64 to vent stripper column 28. In vent stripper column 28, the material is stripped of light ends which exit column 28 via overhead as indicated at 66. The overhead contains primarily methyl iodide, methyl acetate, acetaldehyde and optionally additional permanganate reducing compounds discussed above. Line 66, in accordance with the invention, is directly fed to an aldehyde removal system 90 which includes a distillation column 92 as well as a condenser 94, a receiver vessel 96 and an extractor 98. According to the invention, single-stage, multi-stage, or agitated counter-current extraction may be employed. Likewise, it is apparent that the recovered light ends stream may be purified by distillation, extraction, extractive distillation or combinations of the foregoing.

A salient feature of the present invention is feeding the hot, stripped methyl iodide and methyl acetate directly to distillation column 92 so that the enthalpy of the stream can be used to help purify the stream. In column 92, acetaldehyde and optionally other permanganate reducing compounds are distilled off and exit column 92 via overhead 100. The residue of column 92 thus includes methyl iodide and methyl acetate purified of acetaldehyde impurity and may be returned to the production unit via line 105.

The overhead 100 from column 92 is fed to condenser 94 wherein light ends containing acetaldehyde and optionally other permanganate reducing compounds are condensed and fed to a receiver vessel 96. The condensate from receiver vessel 96 may be further chilled at 102 before being fed to extractor 98. In extractor 98, water is used to extract the aldehyde and other permanganate reducing compounds from the methyl acetate and methyl iodide containing stream. The purified material may be directly returned to the system 10 via line 104, analogously to line 105. For example, the purified material may be returned to receiver vessel 42 and recycled to the light ends and reaction system as shown. Alternatively, the purified material may be returned to a pump serving a heavy phase recycle stream, a pump serving a catalyst recycle stream, or to another dedicated pump providing return to the reactor 12. Such features are readily incorporated into production systems 10 of the class shown.

The system shown in FIGS. 2 and 3 has the advantage over prior art systems, in that the vent stripped methyl iodide and methyl acetate provided in stream 66 has a very high concentration of acetaldehyde relative to other streams available in system 10. The high concentration of permanganate reducing compounds in stream 66 offers the further advantage that because the acetaldehyde and optionally other permanganate reducing compounds are more concentrated, less material must be purified and recycled in order to achieve target purity levels. Furthermore, removing permanganate reducing compounds relatively early in the purification process reduces the opportunities for production of derivative impurities such as crotonaldehydes.

Still another advantage of the invention is that the enthalpy in stripped vapor stream 66 may be used to help remove acetaldehyde from the stream when it is fed directly in gaseous form to column 92. Alternatively, the vent-stripped light ends stream can be condensed to a liquid and then purified if that is more convenient based on available equipment.

Figure 4:
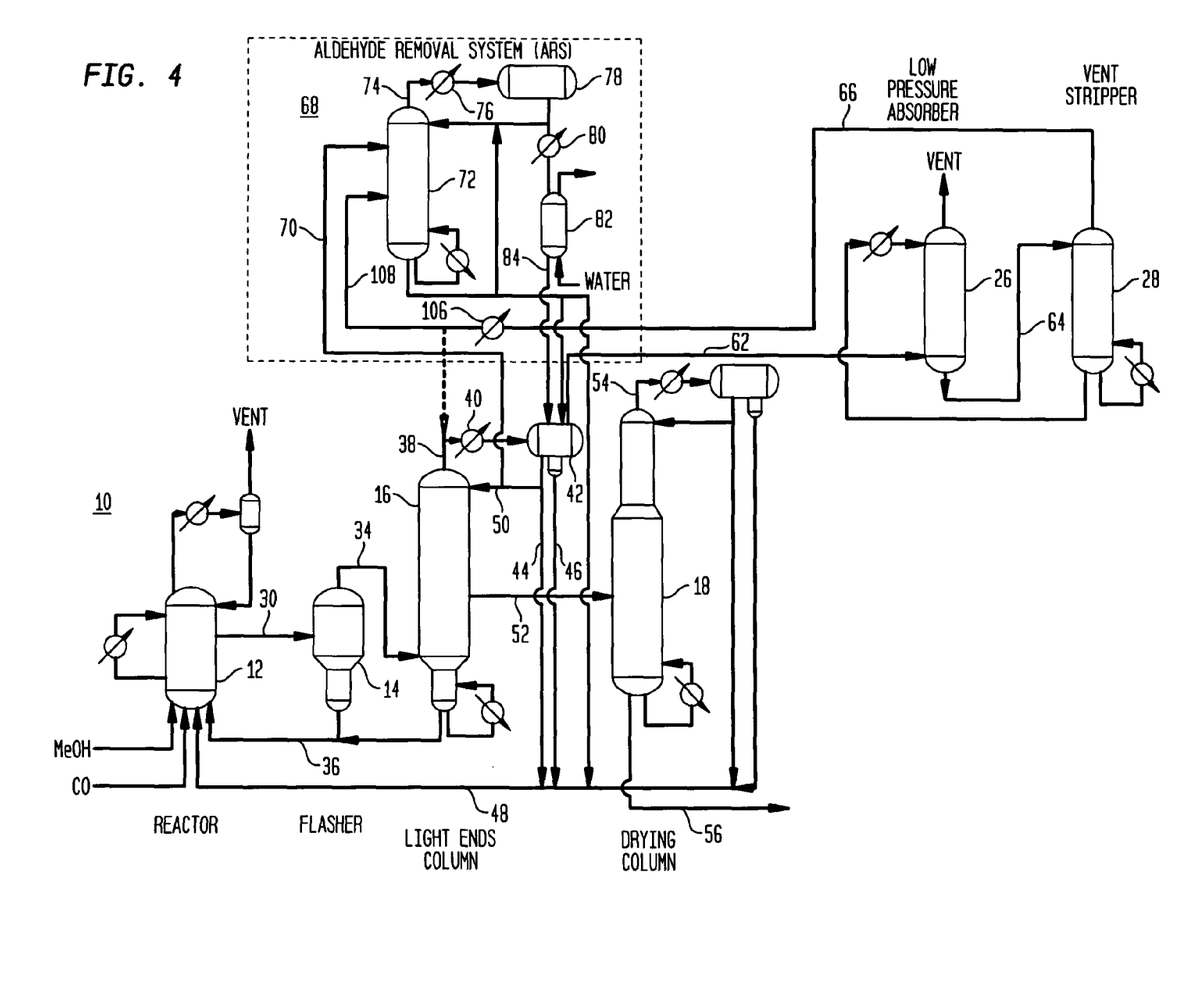
FIG. 4 is a schematic diagram of an alternate construction of an improved methanol carbonylation system of the invention.

In another embodiment of the invention shown in FIG. 4, stream 66 may be fed to an existing aldehyde removal system 68. If desired, the light ends from stripper 28 may be further chilled at 106 before being fed to column 72, if so desired, by way of line 108. Optionally, some of the material in stream 66 may be returned to the light ends column 16.

Figure 5:
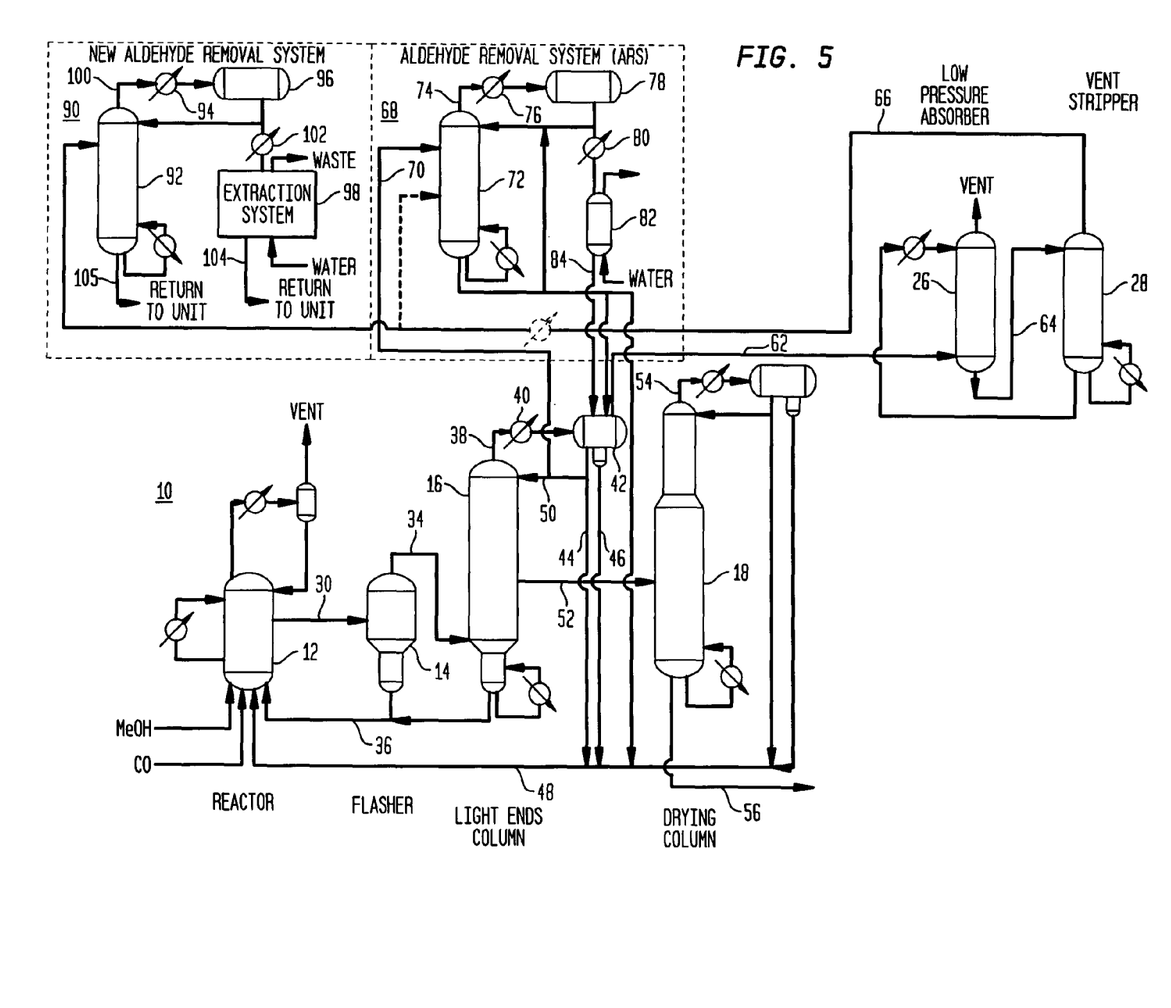
FIG. 5 is a schematic diagram of still another alternate construction of an improved methanol carbonylation system of the invention.

In still yet another embodiment of the invention shown in FIG. 5, the condensed liquid from the receiver vessel is fed via line 70 to a conventional aldehyde removal system, while stripped vapor is supplied via line 66 to aldehyde removal system 90 as shown in the diagram. Optionally, some of the stripped vapor may be sent to an existing aldehyde removal system 68, i.e., at column 72.

One of skill in the art will appreciate that system 10 can be configured in a variety of ways, and may employ different catalysts, promoters and so forth. A Group VIII catalyst metal used in connection with the present invention may be a rhodium and/or iridium catalyst. The rhodium metal catalyst may be added in any suitable form such that rhodium is in the catalyst solution as an equilibrium mixture including [Rh(CO)$_2$I$_2$]$^-$ anion as is well known in the art. When rhodium solution is in the carbon monoxide-rich environment of the reactor, solubility of the rhodium is generally maintained because rhodium/carbonyl iodide anionic species are generally soluble in water and acetic acid. However, when transferred to carbon monoxide depleted environments as typically exist in the flasher, light ends column and so forth, the equilibrium rhodium/catalyst composition changes since less carbon monoxide is available. Rhodium precipitates as RhI$_3$, for example; details as to the form of entrained rhodium downstream of the reactor are not well understood. Iodide salts help alleviate precipitation in the flasher under so-called "low water" conditions as will be appreciated by one of skill in the art.

Iodide salts maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The iodide salt may be added as a mixture of salts such as a mixture of lithium iodide and sodium iodide and/or potassium iodide. Alternatively, the iodide salt may be generated in-situ since under the operating conditions of the reaction system, a wide range of non-iodide salt precursors such as alkali metal acetates will react with methyl iodide to generate the corresponding co-promoter iodide salt stabilizer. Suitable salts can may be generated in situ from non-ionic precursors, such as a phosphine oxide or any suitable organic ligand or ligands if so desired. Phosphine oxides and suitable organic ligands generally undergo quaternization in the presence of methyl iodide at elevated temperatures to yield salts which maintain iodide anion concentration. For additional detail regarding iodide salt generation, see U.S. Pat. No. 5,001,259 to Smith et al.; U.S. Pat. No. 5,026,908 to Smith et al.; and U.S. Pat. No. 5,144,068, also to Smith et al., the disclosures of which are hereby incorporated by reference.

An iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

A supported Group VIII catalyst may be employed if so desired. One preferred system includes an insoluble polymer having pendent pyrrolidone groups which support a rhodium species. One suitable catalyst is a polyvinylpyrrolidone which has been crosslinked and rhodium loaded. Cross-linking can be achieved using a caustic catalyst as disclosed in U.S. Pat. No. 2,938,017 or by using a cross-linking agent such as disclosed in German patent DE 2,059,484. These references are herein incorporated by reference. This catalyst is prepared by reacting the polymer support with an alkyl halide and a rhodium compound. Both reactions are readily accomplished by standard procedures and using known components for such reactions. For example, it is preferred to simply add an amount of the insoluble polymer such as in powder or resin bead form to what otherwise constitutes as the homogeneous medium for the methanol carbonylation reaction. Such carbonylation reaction medium includes methanol and/or methyl acetate, acetic acid and a small amount of water in a pressure vessel along with a rhodium compound and an iodide promoter as described herein. Further details appear in U.S. Pat. No. 5,466,874, the disclosure of which is incorporated herein by reference in its entirety.

Another system includes an insoluble, pyridine ring-containing polymer, and a Group VIII metal supported thereon and is known per se. The term "pyridine ring-containing polymer" used herein is intended to refer to a polymer containing substituted or non-substituted pyridine rings or substituted or non-substituted, pyridine-containing polycondensed rings such as quinoline rings. The substituents include those inert to the methanol carbonylation such as an alkyl group and alkoxy group. Typical examples of the insoluble, pyridine ring-containing polymers include those obtained by reaction of vinylpyridine with a divinyl monomer or by reaction of vinylpyridine with a divinyl monomer-containing vinyl monomer, such as copolymers of 4-vinylpyridine and divinylbenzene, copolymers of 2-vinylpyridine and di-vinylbenzene, copolymers of styrene, vinylbenzene and divinylbenzene, copolymers of vinylmethylpyridine and divinylbenzene and copolymers of vinylpyridine, methyl acrylate and ethyl diacrylate. Further details appear in U.S. Pat. No. 5,334,755, the disclosure of which is incorporated herein by reference in its entirety.

Methyl iodide is used as the promoter. Preferably, the concentration of methyl iodide in the liquid reaction composition is in the range 1 to 50% by weight, preferably 2 to 30% by weight.

The promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The carbonylation apparatus or process that is the subject of the invention typically includes a reactive section, purification section, a catalyst reservoir system and a light ends recovery system. The present invention may be appreciated in connection with, for example, the carbonylation of methanol with carbon monoxide in a homogeneous catalytic reaction system comprising a reaction solvent (typically acetic acid), methanol and/or its reactive derivatives, a soluble rhodium catalyst, and at least a finite concentration of water. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure of the carbonylation reaction is suitably in the range 10 to 200 Bar, preferably 10 to 100 bar, most preferably 15 to 50 Bar. The temperature of the carbonylation reaction is suitably in the range 100 to 300° C., preferably in the range 150 to 220° C. Acetic acid is typically manufactured in a liquid phase reaction at a temperature of from about 150-200° C. and a total pressure of from about 20 to about 50 bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range 0.1 to 16% by weight, more preferably 1 to 14% by weight, most preferably 1 to 10% by weight.

The invention provides in one embodiment a method of making acetic acid while controlling aldehyde and aldehyde-derived impurities comprising: (a) carbonylating methanol or reactive derivatives thereof in a reactor of a production system in the presence of a Group VIII metal catalyst and a methyl iodide promoter while maintaining a concentration of water in the reactor of from 1-10% by weight of the reaction medium and concurrently maintaining in the reactor a predetermined partial pressure of carbon monoxide; (b) venting non-condensibles from the production system so as to provide vent gas containing light ends and aldehyde impurity; (c) feeding the vent gas from the production system to an absorber tower; (d) supplying a scrubber solvent to the absorber tower, the scrubber solvent comprising acetic acid, methanol, methyl acetate or mixtures thereof; (e) contacting the vent gas with the scrubber solvent thereby removing light ends and aldehyde impurity from the gas and absorbing into the scrubber solvent; (f) stripping absorbed light ends and aldehyde impurity from the absorber solvent to provide a vent-recovered light ends stream; (g) purifying the vent-recovered light ends stream to remove aldehyde impurity; and (h) recycling purified light ends from the vent-recovered light ends stream to the production system. The Group VIII metal catalyst may be a rhodium catalyst or an iridium catalyst and the concentration of water in the reactor may be maintained at from 2-8% by weight of the reaction medium. Generally speaking, the vent-recovered light ends stream is purified by distillation, extraction, extractive distillation or combinations thereof prior to recycling light ends to the production stream.

While the invention has been illustrated in connection with particular examples, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. An improved method of operating an apparatus for making acetic acid of the class including a production system having a reactor containing a reaction medium and a product purification train, wherein the production system is vented to an absorber tower, the improvement comprising:
    (a) scrubbing light ends and aldehyde impurity from vent gas with an absorber solvent;
    (b) stripping absorbed light ends and aldehyde impurity from the absorber solvent to provide a vent-recovered light ends stream;
    (c) purifying the vent-recovered light ends stream to remove aldehyde impurity; and
    (d) recycling purified light ends from the vent-recovered light ends stream to the production system.

2. The improvement according to claim 1, wherein the aldehyde impurity comprises acetaldehyde.

3. The improvement according to claim 1, wherein the light ends comprise methyl iodide.

4. The improvement according to claim 1, wherein the light ends comprise methyl acetate.

5. The improvement according to claim 1, wherein the absorber solvent comprises acetic acid.

6. The improvement according to claim 1, wherein the absorber solvent comprises methanol.

7. The improvement according to claim 1, wherein the vent-recovered light ends stream is purified by distillation.

8. The improvement according to claim 1, wherein the vent-recovered light ends stream is in the vapor phase and is fed to a refluxing distillation tower.

9. The improvement according to claim 1, wherein the vent-recovered light ends are purified of aldehyde impurity by extraction with water prior to recycling to the production unit.

10. The improvement according to claim 1, wherein the reaction medium contains a rhodium or iridium catalyst and a concentration of water from 1-10% by weight.

11. An apparatus for producing acetic acid comprising:
    (a) a reactor for carbonylating methanol or its reactive derivatives, the reactor containing a catalyst selected from rhodium catalysts, iridium catalysts and mixtures thereof in an acetic acid reaction mixture;
    (b) a flash system configured to receive a stream of the acetic acid reaction mixture and separate it into (i) at least a first liquid catalyst recycle stream, and (ii) a crude process stream containing acetic acid;
    (c) a first distillation column coupled to the flash system, the first distillation column being adapted to separate low boiling components from the crude process stream, and generate a purified process stream, the first distillation column and optionally the reactor and flash system also operating to generate a vent gas stream comprising light ends and aldehyde impurity;
    (d) an absorber tower adapted for receiving the vent gas stream and removing light ends and aldehyde impurity therefrom with a scrubber solvent;
    (e) a stripping column coupled to the absorber tower for stripping light ends and aldehyde impurity from the scrubber solvent to generate a vent-recovered light ends stream including aldehyde impurity; and
    (f) an aldehyde removal system coupled to the stripping column for receiving the recovered light ends stream and removing aldehyde impurity therefrom.

12. The apparatus according to claim 11, wherein the aldehyde removal system comprises a distillation column.

13. The apparatus according to claim 11, wherein the aldehyde removal system comprises an extraction unit.

14. The apparatus according to claim 11, wherein the aldehyde removal system includes a distillation column and an extraction unit.

15. The apparatus according to claim 11, further comprising a drying column coupled to the first distillation column for receiving the purified process stream and removing water therefrom.

* * * * *